United States Patent
Kondapi

(10) Patent No.: US 7,927,831 B2
(45) Date of Patent: Apr. 19, 2011

(54) ANTI HIV-1 BACTERIAL AND BACULOVIRUS RECOMBINANT EPAP-1

(75) Inventor: Anand K. Kondapi, Hyderabad (IN)

(73) Assignees: The Secretary, Department of Biotechnology (IN); University of Hyderabad (IN)

( * ) Notice: Subject to any disclaimer, the term of this patent is extended or adjusted under 35 U.S.C. 154(b) by 743 days.

(21) Appl. No.: 11/885,128

(22) PCT Filed: Jun. 15, 2006

(86) PCT No.: PCT/IN2006/000204
§ 371 (c)(1),
(2), (4) Date: Aug. 27, 2007

(87) PCT Pub. No.: WO2007/074471
PCT Pub. Date: Jul. 5, 2007

(65) Prior Publication Data
US 2008/0145896 A1    Jun. 19, 2008

(30) Foreign Application Priority Data
Dec. 26, 2005   (IN) .......................... 3477/DEL/2005

(51) Int. Cl.
*C12P 21/06*  (2006.01)
*C12N 15/00* (2006.01)
*C12N 1/20*  (2006.01)
*C07H 21/02* (2006.01)
*C07K 1/00*  (2006.01)

(52) U.S. Cl. ................. 435/69.1; 435/320.1; 435/252.3; 530/350; 536/23.1

(58) Field of Classification Search ................. 435/69.1, 435/320.1, 252.3; 530/350; 536/23.1
See application file for complete search history.

(56) References Cited

FOREIGN PATENT DOCUMENTS
IN         191075         9/2003

OTHER PUBLICATIONS

Kelvin Y. Kwan et al.; "Mice lacking DNA topoisomerase IIIβ develop to maturity but show a reduced mean lifespan"; Department of Molecular and Cellular Biology, Harvard University, Cambridge, MA; PNAS, May 8, 2001, vol. 98, No. 10, pp. 5717-5721.
Secondo Sonza et al.; "Human Immunodeficiency Virus Type 1 Replication Is Blocked prior to Reverse Transcription and Integration in Freshly Isolated Peripheral Blood Monocytes"; Journal of Virology, Jun. 1996, vol. 70, No. 6, pp. 3863-3869.
Kondapi et al., "Anti-HIV activity of glycoprotein from first trimester placental tissue", Antiviral Research, (2002), vol. 54, pp. 47-57.
Saiki et al., "Primer-Directed Enzymatic Amplification of DNA with a Thermostable DNA Polymerase", Science, (Jan. 29, 1988), vol. 239, No. 4839, pp. 487-491.

*Primary Examiner* — Maryam Monshipouri
(74) *Attorney, Agent, or Firm* — The Webb Law Firm

(57) ABSTRACT

The invention relates to an anti HIV-1 active recombinant Epap-1 expressed in bacterial and baculovirus which significantly binds to gp120 of HIV-1 virus isolates.

16 Claims, 17 Drawing Sheets

Figure 1

Binding of 90 KDa Epap-1 to *Sambucus nigra* bark Lectin, hence it is a glycoprotein SDS-PAGE AND WESTERN BLOT ANALYSIS OF Epap-1

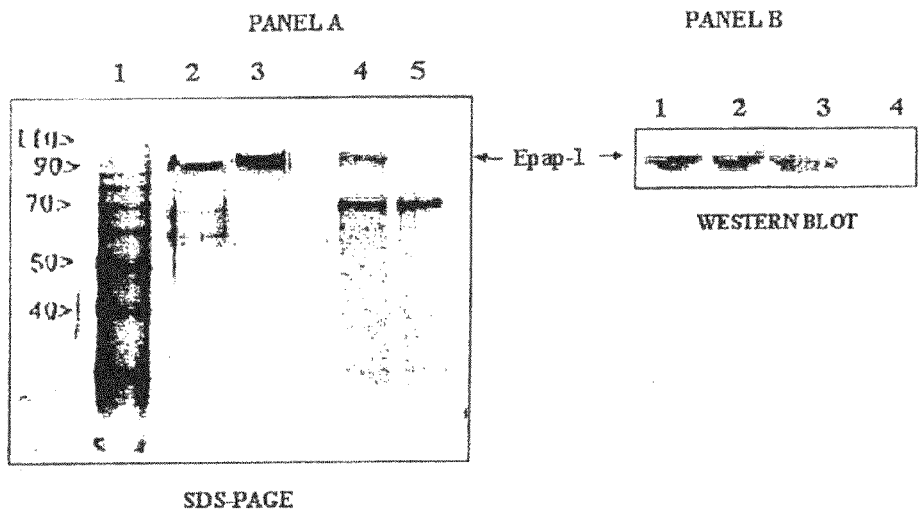

PANEL A: 10% SDS PAGE

Lane 1: Molecular weight marker (10kDa ladder)
Lane 2: 40-80% ammonium sulphate precipitated protein
Lane 3: Epap-1
Lane 4: Unbound protein fraction
Lane 5: Phosphate buffer wash (pH 6.0)

PANEL B: WESTERN BLOT

Lane 1: 40-80% ammonium sulphate precipitated protein
Lane 2: Epap-1
Lane 3: Unbound protein fraction

Elution 60 KDa protein from Leupeptin bound 90 KDa Epap-1

10%SDS PAGE

Lane 1: Epap-1 eluted with phosphate buffer (pH 6.0)
Lane 2-5 Unbound protein fraction
Lane 6: 40-80% ammonium sulphate precipitated protein Rec Bacterial Epap-1 do not Bind to *Sambucus nigra* lectin, hence it is not a glycoprotein.

Rec Bacterial Epap-1 binds to Leupeptin like native Epap-1, elutes a 47 kDa protein at pH 6.

Figure 4 A

Preparation of recombinant baculovirus harboring his-tagged Epap-1 and their expression in *Sf9* insect cells Step 1: Epap-1 λ gt11-cDNA is PCR amplified using λ gt11 forward and reverse primer & released inserts will be sequenced.
Step 2: PCR amplified inserts are cloned into TA vector (pG105T) vector.
Step 3: Epap-1 cDNA from pG105T vector is isolated and cloned into SaI-1-SacI pFast Bac HT vector.
Step 4: DH10 Bac cells are transformed with the pFast Bac HT vector.
Step 5: Transposition of the expression casette from the donor plasmid to the Bacmid DNA.
Step 6: Isolation of Recombinant Bacmid DNA.
Step 7: Transfection of *Sf9* insect cells.
Step 8: Expression and purification of recombinant his-tagged Epap-1 protein.

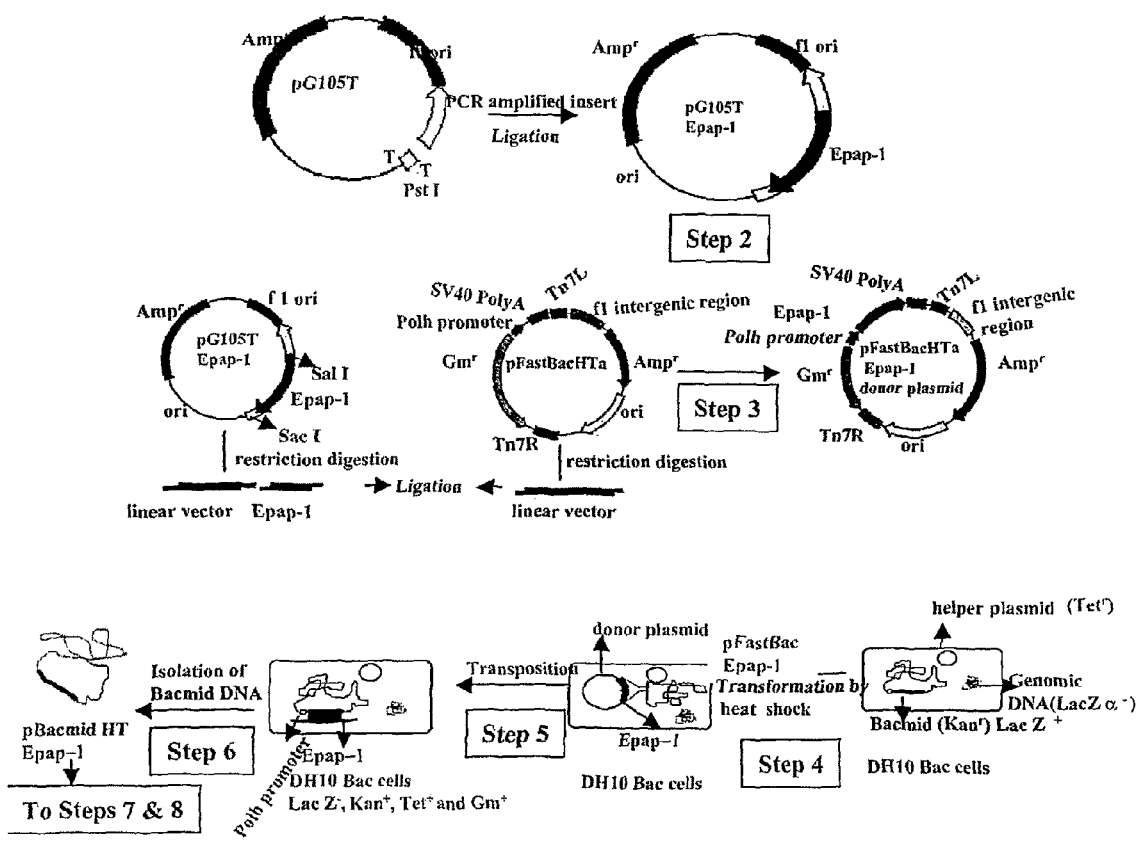

Figure 4 B

Recombinant Epap-1 expressed using Baculovirus system in SF9 cells

Expression and Purification of 6xHis-tagged proteins from Baculovirus infected Insect cells under native conditions

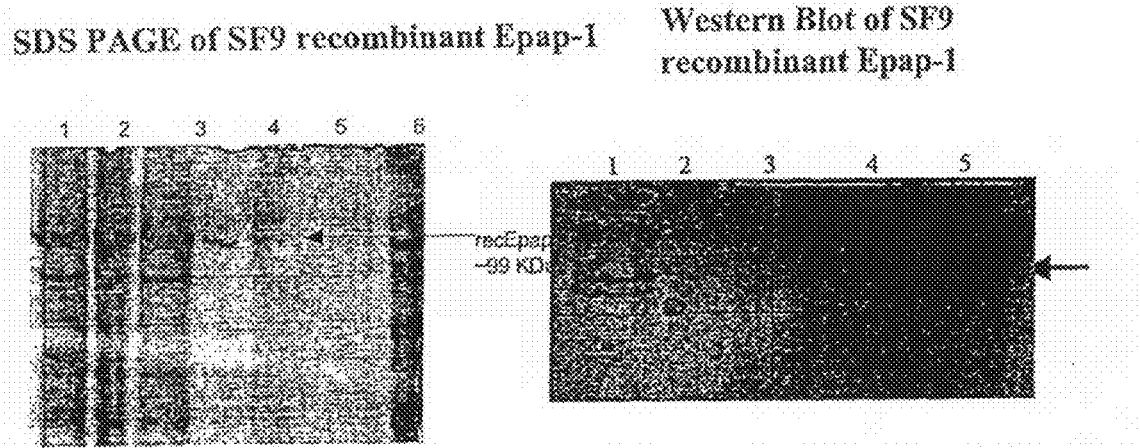

SDS PAGE of SF9 recombinant Epap-1

Western Blot of SF9 recombinant Epap-1

LANE 1  Input of SF 9 expressed protein extract loaded onto Ni affinity Matrix.
LANE 2  flow through fraction
LANE 3  Wash fraction
LANE 4  Elute fraction containing baculovirus Epap-1
LANE 5  Elute fraction containing baculovirus Epap-1
LANE 6  Elute fraction
LANE 7  90 KDa Marker Lane 1: Input of infected SF9 cell lysate loaded on to Ni-NTA agarose
Lane 2: flow thru fraction]
Lane 3: Elute
Lane 4: cell debris
Lane 5: Input of infected SF9 cell lysate loaded on to Ni-NTA agarose ~99 KDa Includes 16 KDa HisTag. Net Mol Wt of recBaculoEpap-1 is ~83 KDa Purification being optimized to increase the stability and yield of Epap-1.

Figure 5 A

Preparation of recombinant his-tagged Epap-1 and their expression in BL-21 pLyse E. coli cells Step 1: Epap-1 λ gt11-cDNA is PCR amplified using λ gt11 forward and reverse primer &released inserts will be sequenced.
Step 2: PCR amplified inserts are cloned into TA vector (pG105T) vector.
Step 3: Epap-1 cDNA from pG105T vector is isolated and cloned into KpnI-SacI sites of pETHTa vector.
Step 4: DH5 alpha E.coli cells were transformed with the pETHTa-Epap-1 vector.
Step 6: Isolation of Recombinant plasmid DNA.
Step 7: Transformation into BL-21 pLyse cells.
Step 8: IPTG induced expression and purification of recombinant his-tagged Epap-1 protein.

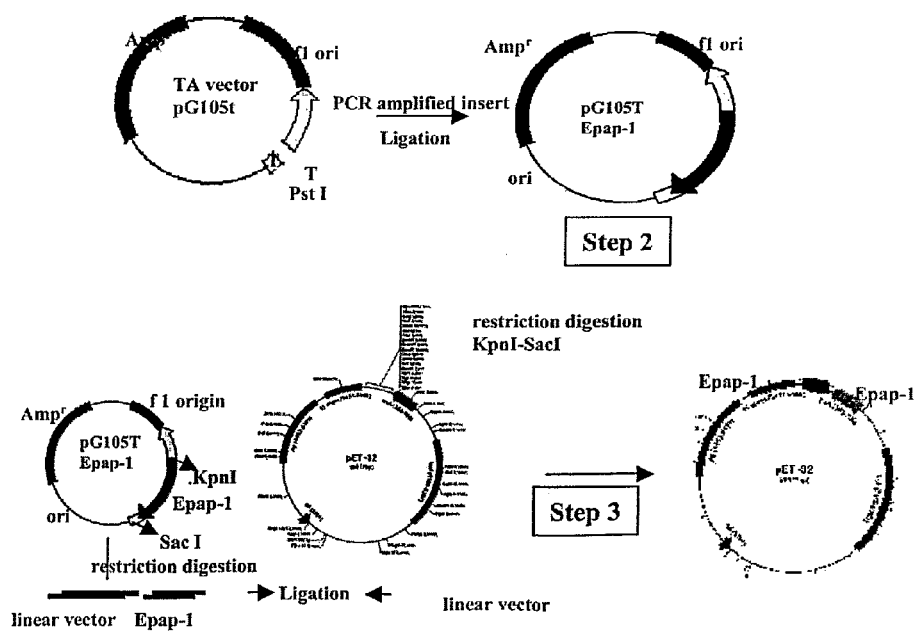

Figure 5 B

Recombinant Epap-1 expressed using Bacterial system in *E.coli*

A

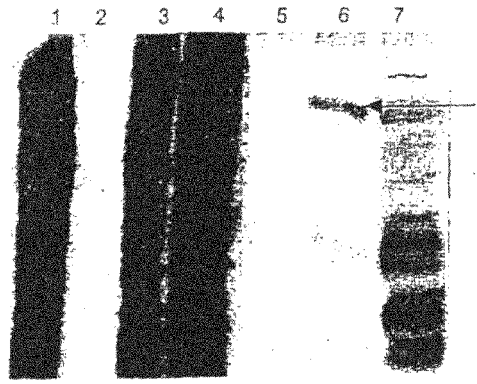

Bacterial Rec Epap-1~99KDa

LANE 1  Input of HTa expressed bacterial protein extract loaded onto Ni affinity Matrix.
LANE 2  empty well
LANE 3  flow through fraction
LANE 4  Wash Fraction
LANE 5  Wash fraction
LANE 6  Elute fraction containing bacterial Epap-1
LANE 7  Marker ~99 KDa Includes 16 KDa HisTag. Net Mol Wt of recBacterialEpap-1 is ~83 KDa

B

Western Blot Analysis with Monoclonal His Tag Antibody

LANE 1-3  Elute fraction of bacterial Epap-1 probed with His Tag Monoclonal Antibody.

← Bacterial Epap-1

Western Blot Analysis with Polyclonal Epap-1 Antibody

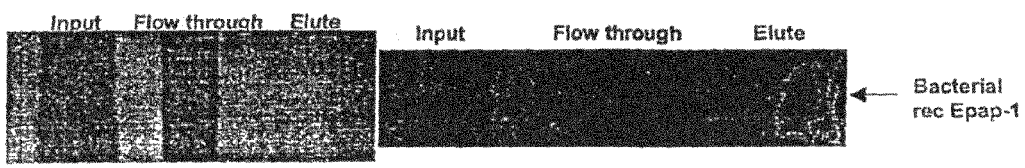

← Bacterial rec Epap-1

| S.No | Bacterial Lysate loaded on to Ni-NTA Column | Elutes of Ni-column | % Yield |
|---|---|---|---|
| 1. | 10.7mg/ml | 0.65mg/ml | 6% |

Figure 6

Epap-1 and gp120 Binding assay

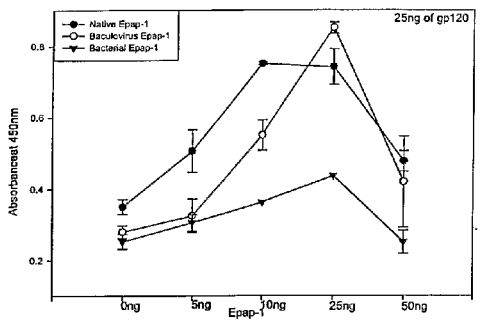 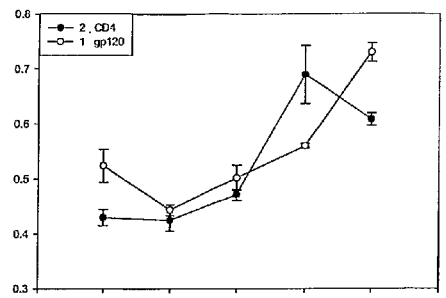

Coat gp120 (25ng) overnight at 4°C

↓ wash thrice with PBST(.15%Tween)

Block with 3% BSA for 2 hr at 37°C

↓ wash thrice

Add Epap-1(0,5,10,25 and 50ng) +Whole gp120 antibody and incubate for 1hr at 37°C ↓ wash thrice Add Rabbit Epap-1 Polyclonal antibody (1:1000) incubate for 1hr at 37°C ↓ wash thrice Add Anti-Rabbit Peroxidase conjugated antibody (1:2000)

incubate for 1hr at 37°C

↓ wash thrice

Add Substrate TMB/$H_2O_2$ and stop reaction with 1N HCl.

Read Absorbance at 450nm

1 Coat gp120 (25ng) overnight at 4°C/
2 Coat CD4(25ng) overnight at 4°C

↓ wash thrice with PBST(.15%Tween)

Block with 3% BSA for 2 hr at 37°C

↓ wash thrice

1 Add CD4 (0,5,10,25 and 50ng) incubate for 1hr at 37°C
2 Add gp120 (0,5,10,25 and 50ng) incubate for 1hr at 37°C ↓ wash thrice Add 1 Mouse CD4 Monoclonal antibody (1:1000)
2 Mouse gp120 Monoclonal antibody (1:1000) incubate for 1hr at 37°C ↓ wash thrice Add Anti-Mouse Peroxidase conjugated antibody (1:2000) incubate for 1hr at 37°C ↓ wash thrice Add Substrate TMB/$H_2O_2$ and stop reaction with 1N HCl.

Read Absorbance at 450nm

Anti-viral activity of Native and recombinant Epap-1 against an Indian HIV-1 isolate Anti-viral activity of Native and recombinant Epap-1 against an Indian HIV-1 isolate

Virus Entry Bioassay

Figure 9B
Action of Native and Recombinant Epap 1 on gp120 Mediated virus entry at 30 min
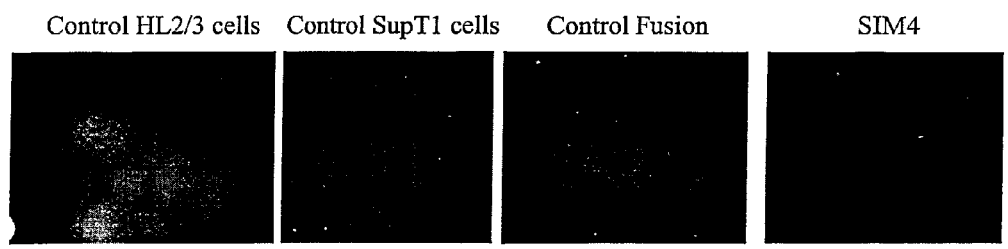
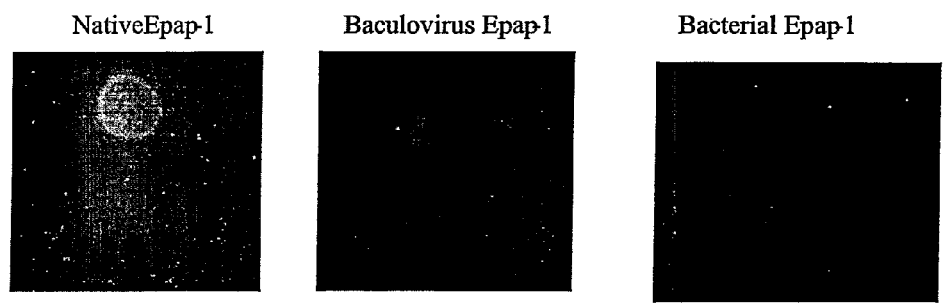
Fusion Reaction in 30 minutes
Fusion Reaction in 30 minutes
Calcein AM loaded HL2/3 in bright green,
Calcein blue loaded SupT-1 appearing in dull

Action of Native and Recombinant Epap-1 on gp120 Mediated virus entry at 60 min Fusion Reaction in 60 minutes Calcein AM loaded HL2/3 in bright green,
Calcein blue loaded SupT-1 appearing in dull

Figure 9 D

Action of Native and Recombinant Epap-1 on gp120 Mediated virus entry at 120 min Fusion        SIM4 Antibody Native.Epap1    Baculovirus Epap1    Bacterial Epap1

Fusion Reaction in 120 minutes

Calcein AM loaded HL2/3 in bright greenish yellow,
Calcein blue loaded SupT-1 in dull

Figure 10

Action of Native and recombinant Epap-1 on viral entry assessed by proviral DNA synthesis

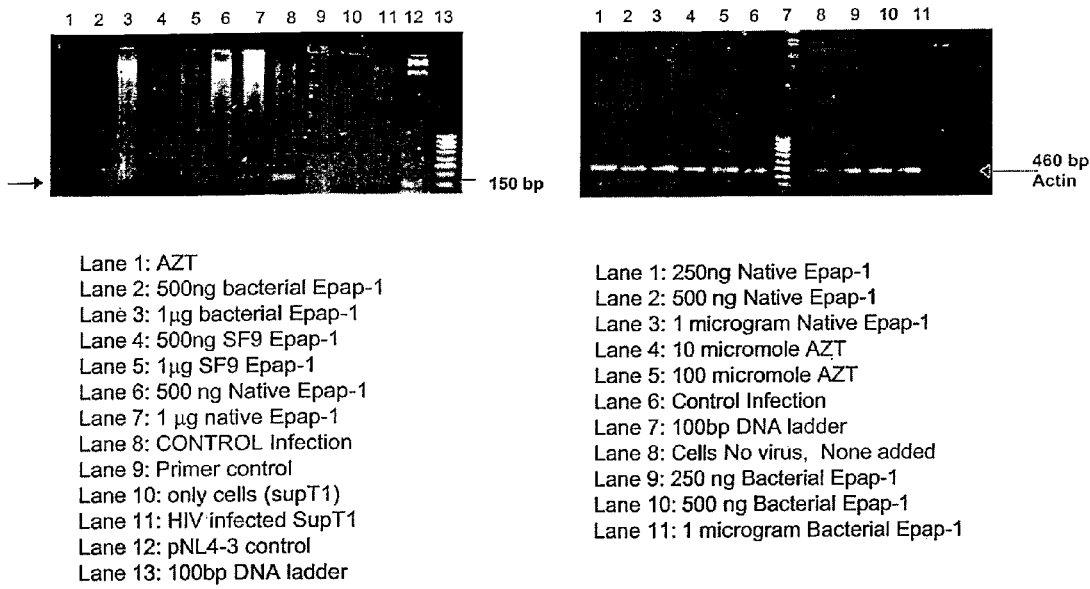

Lane 1: AZT
Lane 2: 500ng bacterial Epap-1
Lane 3: 1µg bacterial Epap-1
Lane 4: 500ng SF9 Epap-1
Lane 5: 1µg SF9 Epap-1
Lane 6: 500 ng Native Epap-1
Lane 7: 1 µg native Epap-1
Lane 8: CONTROL Infection
Lane 9: Primer control
Lane 10: only cells (supT1)
Lane 11: HIV infected SupT1
Lane 12: pNL4-3 control
Lane 13: 100bp DNA ladder Lane 1: 250ng Native Epap-1
Lane 2: 500 ng Native Epap-1
Lane 3: 1 microgram Native Epap-1
Lane 4: 10 micromole AZT
Lane 5: 100 micromole AZT
Lane 6: Control Infection
Lane 7: 100bp DNA ladder
Lane 8: Cells No virus, None added
Lane 9: 250 ng Bacterial Epap-1
Lane 10: 500 ng Bacterial Epap-1
Lane 11: 1 microgram Bacterial Epap-1

Action of Epap-1 native, baculovirus and bacterial recombinant on HIV-1 proviral DNA synthesis:

Cells were challenged with virus in presence of Epap-1 as indicated. The infection was continued for 5 hours.The proviral DNA synthesised in situ was analyzed by lysis of cells following treatment with RNase I and Proteinase K. The presence of proviral DNA was analyzed by PCR amplification of 150 bp gag region using SK38 and SK39 primers.

Figure 11

Molecular action of Native and Recombinant Epap-1 against a constant epitope C5 of virus surface exposed gp120 is conserved among 4 virus isolates tested 0.2 million 3T3 CD4 cells were seeded and fixed in the wells, then blocked with 3% BSA + 2% NGS
↓

HIV-1 virus-Epap-1 complexes were formed in multi well plate, then transferred to the above wells.
↓

The gp120 epitopes unmasked by Epap-1 in captured complexes were detected using indicated monoclonal antibodies against gp120 and Detected with anti-mouse IgG conjugated with peroxidase and TMB substrate system.

ORIGIN
```
   1 GAAAAAAACT GAACCCGCGT TAGACTCCTT TAATGAGCAG CTGTTAAGAA AGTACTTCAG
  61 CTGCGTAGCA AAAATACACA AATTGCGAGC GAACTCCGAG CCGATGGAGA CAGAACGCTA
 121 TCAGCAACCA CAAACACAAC GCGAGCCCAA TGGCTTTTTT TTTTTAGTTC GCCAGTCCAC
 181 AACTCGACAT ACAACAACCT AGTACCACAC CCGTAAGTGC CAGCAAGTTT GTAGCCGCTG
 241 GACGACATTC GACTCGCACC TCGTCGAAAT ACGGCGTCCG TAGCACAACC CGCTAGAGCT
 301 ATGGGTAGCA CCACGACGTA CTCCAGCTAA TTAGTCATAA ATAGAAGTAG TGGACAGGTC
 361 TCCCTCATAC CGATTACGCC ATGAACGTGA ACGTCGTTGC TAGCCACTGG AACTAGGATG
 421 TCGGCGTACG CACTAGTCAG AAGTAGTAGT CGGCCCGCAC AAGGTATAGC CACTCCACCA
 481 CAGCGTAGTC GAGACTGCGC GTCCGAGTTG CGAGAAATCG CTGGTCCACC TCGCCGCAAT
 541 CACAAGCTAT TAGGTGGTAG CCGCTGGATG TTGGTAGGAG GAAGTAATAA ACGCAGTTCG
 601 CTCTACCGAC CAGTAGAACC AAGTAATGAC TCGACAGGCC CGGAGAGAAG ACGATGGAAG
 661 CCGTACGTCG TCCGAGCGCC CAGGTCGGAG ACAAACCGGC CGACTACAAA GCTGTAAGAT
 721 CCTAGTAACT GGTGAGTACT CACTCCCTGA AAGTCGTGCT GGGAAACTAG CCAGTAGGTC
 781 GCACGTTACA TCCGACGAAC CTGATTACTC GAAGTACCGA CACCCCTAGC TCGCTACGTA
 841 ACTCGCGCAT ACAGACCCGC TACAATACCA ACCGATTCTG ATACACACAT GGGTAGTTAC
 901 TGCGTGGCAT ATGGAAGTAA TCTTCATACA CAGTTCAGTC CGACGGACCC GTCCGTCAAA
 961 CGAGAAGGAC ACGCCCGCAC CCAACCACCC ATCCACCACT AGCCTCGGCC GATCAGGTTC
1021 ACACAGACAC GCATGGTCAC CAGCACGCAC GCAGCTTGCG AACCTCACCT TGCCTACGTC
1081 AGAATACGAC AACATTCGCC TTGTCCACGG TGGGTTCACA GTACATCAGG TCCACTGTCG
1141 AATACAACAA CATCCGTTCA GCTGGAGATC CACGTGCGCG CTCAGCGCAG GGACGGCTAA
1201 AGCTTACGCA ACGCGCTCCC TACAGCACCG CGTAGTGTAT CGGATACTGC ACGATTACCG
1261 CGCGGTAAGG AACAGGATTA CGACTACAGT ACGCGTTCCG GAAACGCTAC CGTACCGAGA
1321 CCACTAAAGA TCACGAGCTT CGCACACAGT TCCAGAGTCA GCGTTCACTC AAAACGTTAC
1381 CTTGCAAAGC TCCTTGGAAC AAGCCCAGTA AGCCAAAAAA CAACATGAAG CATGTGGCAG
1441 GAACTTCTTG AACTTGAACA ATGGTAAGGG GGCCTGGGTT TTTTTACTGG CTGGAAAGTG
1501 CCATAACCAC GCCTCTTATA CTTTTGGGCA ATGACTATAA GGACCGTTAT AATCGTGAAA
1561 AGTGTTACCG AGAACCCCAA CCAACTGTTC CTAGAAACCA CTGGATCTCT CTATTAAGCC
1621 ACAACAACTT TGGTGCATGA ACTGTGTCAA CATCACACGC CAGTCAATAC ACATTCATCC
1681 ACCACCACCA AGGGGGGAGA AAGTTCACCG AAACGGACAC TCAAGATAAT GGGACCCGAG
1741 TGGTGGCACC AAAATGTGCA TCACCCCACT ACCGAGAGAG AATCTCACGG CTCTATTAAC
1801 CAAAGGGGGG GCCACGCTGG TGATCCCTCT TTTTTGTTTA GACTTCTAGG GTGGAACCCC
1861 CGTCCACTCG CCTAGTACTC TAGTTGTAGT TGCAGTACTA CTGGAATAGG GGAGGCAAAC
1921 CTGTTCCCAG ATGTTGTAAT CTATTTTTCG TACTACTCTT CCTGCCCCAA ACJTTTGGAC
1981 GCGGATGGTG AATACGTTTT ACCTTGCCAT ACGCCCTTGG TAAAAGTACT CCTCGTAGCT
2041 CGGCGTCGTA CGTACTAACT CGCCGGTTTA CTACGTGGTC CGATCTCGGT GGTTGCTCCT
2101 CTTTCGACCG ACGCCCCATA GTNCTTCGTC GGTTACGCCT ACCGTAGTTC CGAGGTCGTC
2161 CGTTCGCTAG TTGGTAATTC CGTACGGACG TTTGTTCCTA CCGACAGTCC TTCCACCGCC
2221 CTACCGTACG TACCTTACGG CACAGTGGCA CCGTAGTTCT TTCGATCCGC TAGTTAGTCT
2281 TGACTTAAAG TACGTAAGGT TCCTAACGTG TCCACACCCC AGTCCTTTCC
```

Fig. 12

SEQUENCE LISTING

```
<160> NUMBER OF SEQ ID NOS: 1

<210> SEQ ID NO 1
<211> LENGTH: 2237
<212> TYPE: DNA
<213> ORGANISM: Homo sapiens
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (1118)..(1118)
<223> OTHER INFORMATION: n is a, c, g, or t
<220> FEATURE:
<221> NAME/KEY: misc_feature
<222> LOCATION: (2233)..(2233)
<223> OTHER INFORMATION: n is a, c, g, or t

<400> SEQUENCE: 1
gannaaaact gaccccgagn cagactcttt taatgagcag ctgctaagaa agtacttcag      60
ctgcgtagca aaaatacata aactgcgagc gaactccgag gcgatcaaga cagtacgcta     120
tcagcaacca caaacacaac gcgagcccaa aagctttttt tttttttgatc gccagtccac     180 aactcgacat acaacaacct agtaccagtc ccgtaagtac caacaagtct gtatccctg      240 gacgacattc gactcgcacc tcgccgcaat acggcgcccg cagcataacc cgctcttgat     300
atgggtagaa cgccgactta gtcccactaa taacgcacag aaatgaggtg caattagccc     360
tccctcgtac caanttagcc ctcaatatta atatcgtttg cagccaccag aactaagcgg     420
atggcgtaca ccccattcac gtctaatatc gggcctgcat aagatatatg tcactcatcc     480
acgttgaaca cgagaccgct atgatgacga atgatggttc acttggcgac attgtcgctg     540
tcacaagcca gtaatatata tgcgctgaaa gtgggtagat tcaattcata aacgcaggtc     600
gctttacggg ccagtagagc caaataatga cctgacgaga tcgaacagan gctgatgcta     660
ctcgagctta atgaatgcca ccaggtcgga gatcaaccgg ctgactgtca agctacgaaa     720
agcgaatacc tgcggtagga ccatactctg tgaatggttc tagtaccatg gcattcagcg     780
ggcacattac atcccatgaa gccgacaccg cgtactcgct agcgccctgg ttcgcctcac     840
aagatgcacc tggaacgcct ttatacatcc agcctattca tatcctcaaa tttgtacatg     900
acgacgtggg acagggaggt aatttgaata aacagttcag tacgncggac ccgtccttca     960
```

-continued

```
aacgagcagg gcacggtggg atcccaccaa ccctcccacg ttaccccggg cctaggaggt    1020
tcaaacagac ccgcatggtc tccagcccgc tctcaccttc agaacatcac cttgcctacg    1080
tcagaatacg acaacattcg cctagttcac agacggtnca cagtacatca ggtccactgt    1140
cgaatacaac aggttgggtt cagctggaga tccacgtgcg cactcaccgc agcgacggct    1200
aaagcttacg caacgcgctc cctagagcac cgcgtagtgt atcggatatt acacgattac    1260
cgcacagtaa gggacaggat tacgctacg gtacgcgtta cggaaaggct accgtaccga    1320
gaccgctaca gatcacgagc ttcgcccacg ttactgtgca gtaaggaacg gaccgtaagt    1380
tggtggaagg tttgtcggta ggaacccatg cccgtacgga ctcactaagg agcgaatgga    1440
cgacccggga actacgttgc gcgcaccaga cgaagtacca tatggcgtcg aagggatcac    1500
gagtcccgtc tggacaggga gtacgtggta aatcggctgg agatagtccc aaggccatcg    1560
agcaacgagg agtgactttg ccatgggcgt atggcaaggt aaaaaggatc atccttgccc    1620
gatcaatgcg ttgggtctag tagagttgca cggacaatat attcaaacta cttctgggca    1680
tgggtatgcc tcctatattc cactagtagg gccccgacac ctagagtact aggcagatgg    1740
agggcggttc atctcccgag gtctaaacca aaagaggga acgccagcct aacccccgt     1800 ttaataagta gatccgtgcg attctgtctt ggcattgggg tgatgaactt tttggtgcca    1860
ccaatcaggg tctataatct tgactgcctg tttcgttcga tttgtctcca cccttggtgg    1920
tggtggatgg gtgtgtattg acttgtgcgt gattttatca cacttcatgc accatagttg    1980
ttatagttat agtagacata tccagtggtt gtcaggagca gtttgttcag gtatccagca    2040 aaattttca cgacaatacg cggtccttat agtggttgcg ccaaaagtat aatgtgcttg    2100
gttttagtca tttccagcaa gtgaaaaacc ccagggcccc ttaccattgt tcaagttcca    2160
gcagttcctg ccacatgctt catgttggtt tttggcttac tgggcttgtt ccaaggagct    2220
ttgcaaggca acntttt                                                  2237
```

ANTI HIV-1 BACTERIAL AND BACULOVIRUS RECOMBINANT EPAP-1

This application is a National Stage entry of PCT/IN2006/000204, filed Jun. 15, 2006, which claims priority to Indian application 3477/DEL/05 filed Dec. 26, 2005.

FIELD OF INVENTION

This invention relates to an anti HIV-1 active bacterial and baculovirus recombinant Epap-1.

BACKGROUND OF THE INVENTION

Native Epap-1 is an anti-HIV-1 active 90 K.Da glycoprotein isolated from MTP placental tissue that has been purified to homogeneity using single step lectin affinity chromatography. This work has been conducted under a DBT sponsored research project and the process for the purification of native Epap1—has been patented in India in the Indian patent, March 1999 (191075, 21/Del/1999.
1. Native Epap-1 is a glycoprotein
2. It need to be isolated from a natural source, MTP placental tissue
3. Its yield from natural source is not very high.
4. A product from natural source cannot be used as therapeutic or microbicide.

OBJECTS OF THE INVENTION

An object of this invention is to propose a novel anti HIV-1 active recombinant Epap-1.

Another object of this invention is to propose a recombinant Epap-1 which can be used to develop a therapeutic or microbicide against HIV infection.

BRIEF DESCRIPTION OF THE INVENTION

According to this invention there is provided an anti HIV-1 active recombinant Epap-1 expressed in bacterial and baculovirus which significantly binds to gp120 of HIV-1 virus isolates.

BRIEF DESCRIPTION OF THE ACCOMPANYING FIGURES

FIG. 1: shows screening of cDNA library with endlabelled cDNA probe.

FIG. 2: shows clones using gene specific probes and PCR.

FIGS. 3 & 4A-4B shows the recombinant Epap-1 was purified on nickel column.

FIG. 5A-5B shows the purified recombinant protein showing affinity to soluble gp160.

FIG. 6: shows activity of recombinant.

Figure 7:
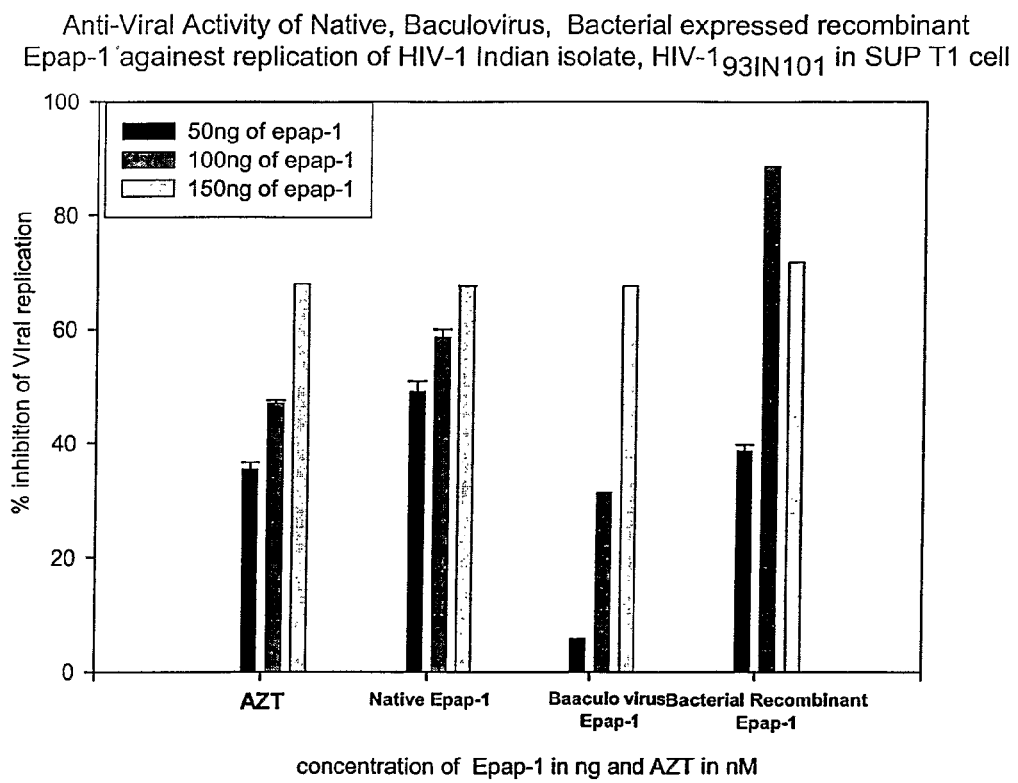

FIG. 7: shows action of native and recombinant Epap-1

Figure 8:
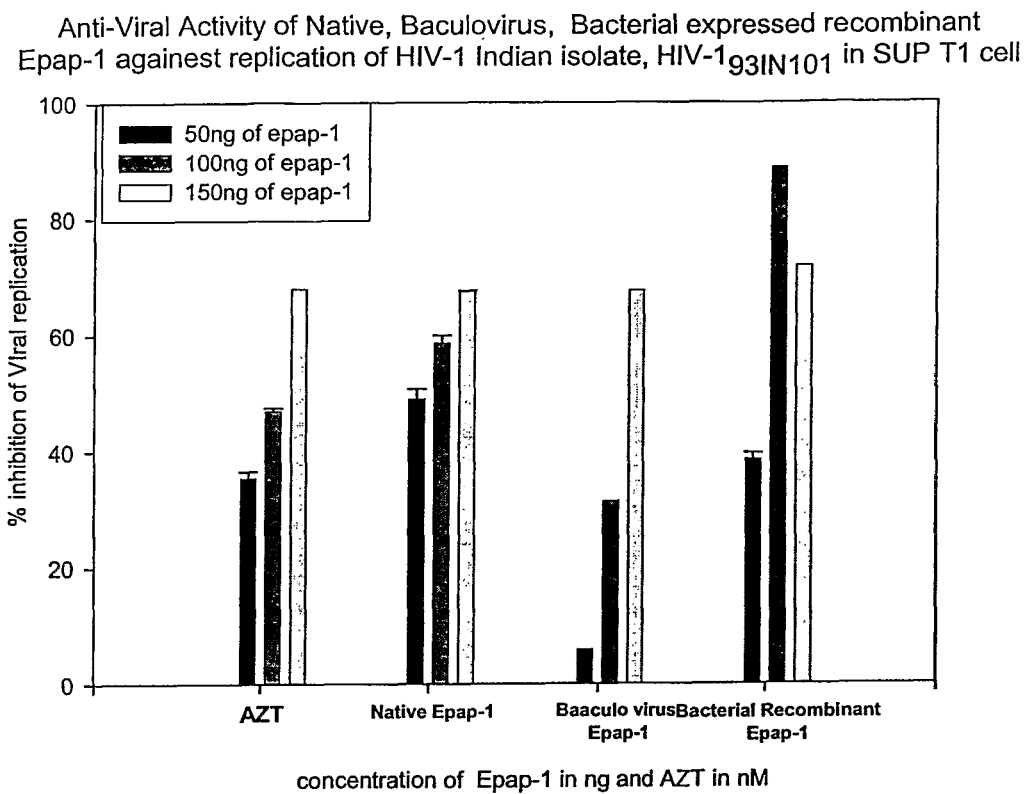

FIG. 8: shows action of Native and recombinant Epap-1 on gp120 mediated virus entry at 60 minutes FIG. 9A-9D shows active of native and recombinant Epap-1 on gp120 mediated virus entry at 120 min.

FIG. 10: shows action of native and recombinant Epap-1 on viral entry assessed by proviral DNA synthesis.

FIG. 11: shows molecular activity of native and recombinant Epap-1 against a constant epitope $C_5$ of virus surface exposed gp120.

FIG. 12: shows the complete DNA Sequence of Epap-1.

DETAILED DESCRIPTION OF THE INVENTION

Figure 2:
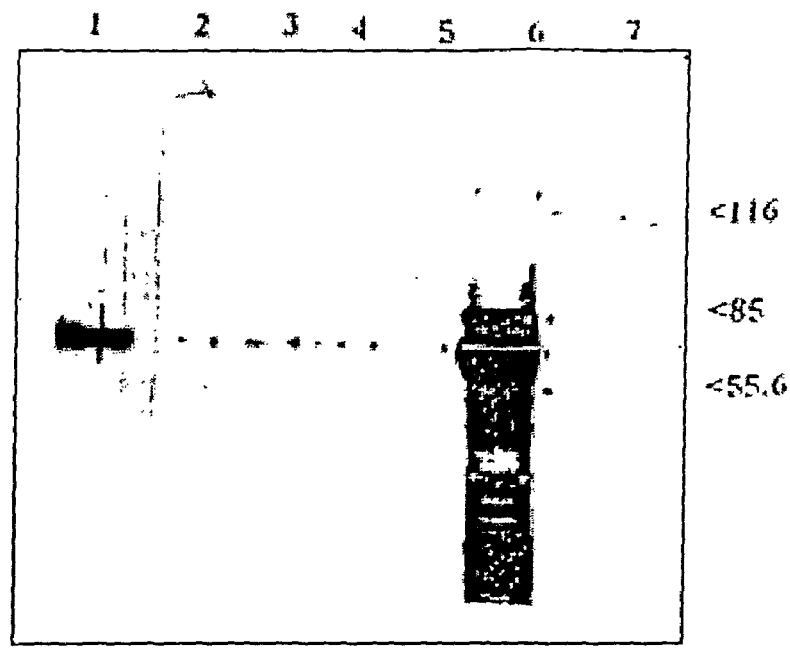

First trimester MTP placental tissue Lamda phage gt11 cDNA library was constructed and screened for cDNA of Epap-1 (FIGS. 1 & 2).

Epap-1 cDNA was isolated, cloned and sequenced.

Figure 3:
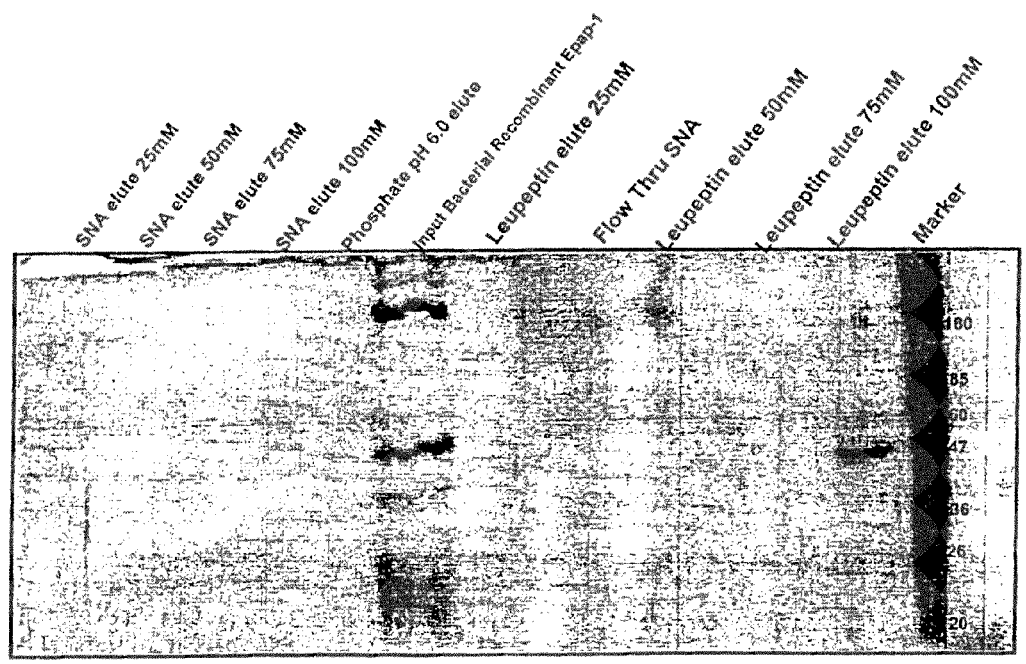

Recombinant Epap-1 was cloned and expressed in Bacterial and Baculovirus systems (FIGS. 3 & 4).

Recombinant Epap-1 significantly binds to gp120 (FIG. 5).

The recombinant Epap-1 proteins show significant anti-HIV-1 activity against HIV-1 Indian Isolate HIV-$1_{93IN101}$ in Sup-T1 (FIG. 6).

Figure 9:
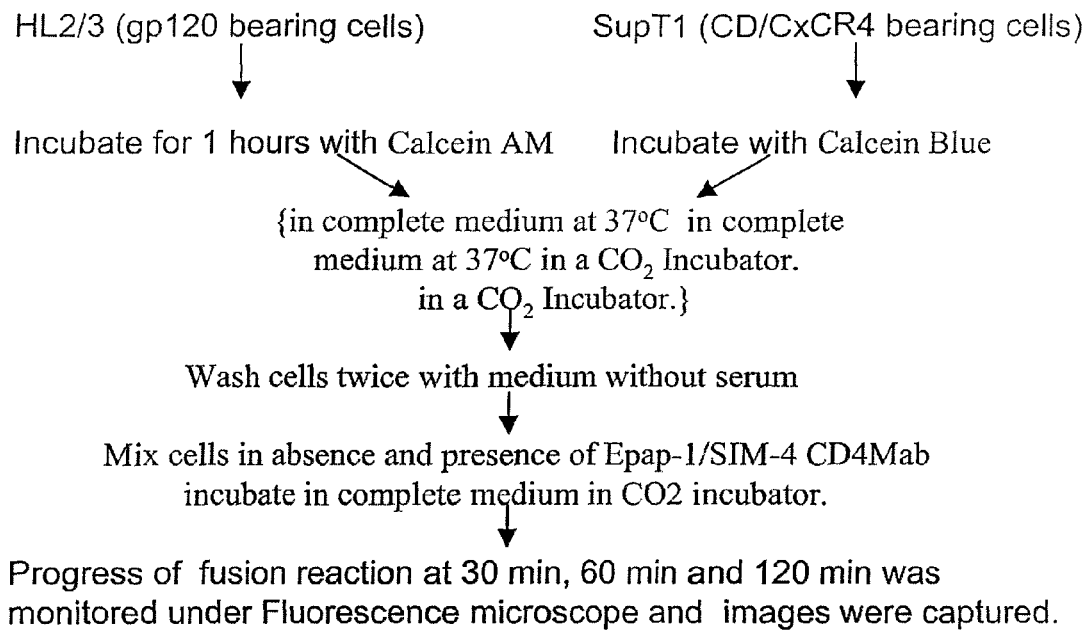
Figure 9:
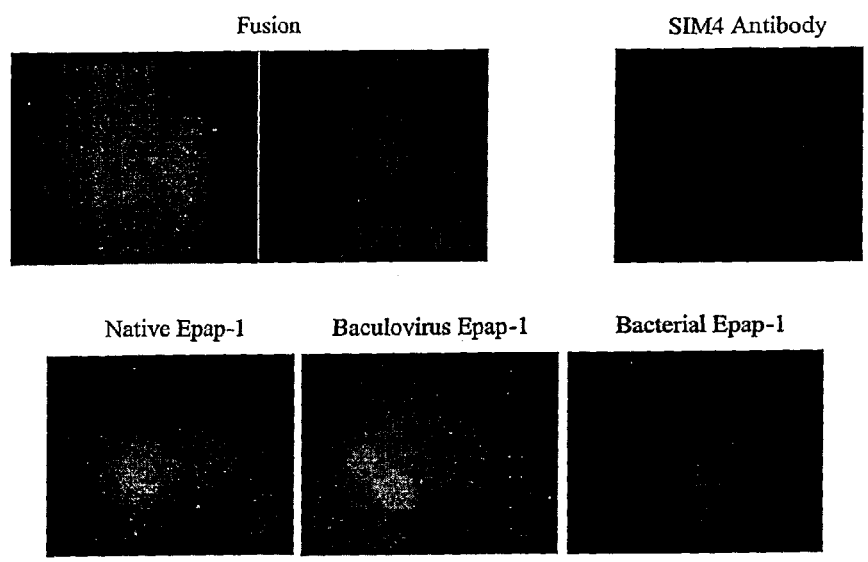

Characterization of Epap-1 action against gp120 mediated viral entry was studied using HL2/3(gp120) and SupT-1 (CD4/CxCR4) cells by fluorescence dye transfer bioassay. The results of these experiments showed that the recombinant Epap-1 proteins can block gp120 mediated fusion reaction confirming that recombinant Epap-1 can block HIV-1 viral entry (FIG. 7-9). This was also confirmed by analysis of proviral DNA synthesis in infection conducted in presence of recombinant Epap-1. (FIG. 10)

In summary, we cloned, expressed Epap-1 in both Baculovirus and Bacterial systems, the recombinant protein retains antiviral activity as well as exhibits similar molecular mechanism of action.

Sequencing of Purified Epap-1.

The N-terminal Seventy amino acids of Epap-1 was sequenced using Shimadzu Automated Sequencer in our University. The Epap-1 sequence was used to design probe for northern detection of Epap-1 encoding mRNA. This probe was used for screening and analysis of cDNA library.

Construction of cDNA Library and Screening of cDNA Library Using Both Radiolabeled Probe and Antibody:

We have constructed MTP placenta tissue cDNA library using λ gt11 phage library construction method. The phage cDNA library was screened with Epap-1 oligo probe (FIG. 1). We have obtained four positive clones. The clones were characterized for the presence of insert by PCR using λ gt11 primers. The PCR amplified product was a ~2.3 Kbp fragment in all the four clones (FIG. 2); the presence of Epap-1 sequence was reconfirmed by southern blot analysis. All the four clones were screened for expression of recombinant Epap-1 in Y1090, using anti-Epap-1 IgG, thus confirming that the clones are indeed positive for Epap-1 protein expression. Clone 4 was selected for cloning and expression of protein. The insert in the clone 4 was PCR amplified using λ gt11 primers, the amplified ~2.3 Kbp product was thymidylated at the ends; then cloned into TA vector. The TA vector cloned insert was further confirmed by PCR as well as southern blotting. The confirmed recombinant TA clone was sequenced using M13 forward and reverse primers (FIG. 2).

Sequencing of Insert DNA of Positive cDNA Clone.

Insert positive DNA was sequenced and complete sequence is provided at (FIG. 12) (SEQ. ID. NO. 1). BlastN analysis of the Epap-1 cDNA suggests that it may not be a single gene product.

Cloning and Expression of Epap-1 in Baculovirus System:

The 5'-end and 3'-end sequence of the insert was analyzed to find its orientation. Based on the orientation, we have cloned the insert into a pFAST bac pack HTa vector in right orientation. For control purpose we have used pFAST bac pack HTb and pFAST bac pack HTc vectors also for cloning. Each of the cloned vectors was transformed into DH5 α bacterial cells and the transformed colonies were screened for the insert-containing vector using PCR. The confirmed recombinant DNA was isolated and transformed into DH10 bac cells. The transposition was screened using X-Gal based blue-white selection.

The Bacmid DNA was isolated from the white colonies. The isolated Bacmid DNA was transfected into SP9 cells using lipofectamine method. The transfected SF9 cells were scored for the Baculovirus production. The produced Baculovirus was assayed for MOI. The recombinant virus was propagated for 48 hours and used for the production of recombinant Epap-1.

Expression of Epap-1 in Baculovirus

The adhering SF9 cells were infected with recombinant Baculovirus at MOI of $2\times10^7$, the suspension of infected cells at 72 hours was harvested and lysed. The expressed protein was purified from the homogenate using Ni-affinity chromatography. The purified protein profile is shown in FIG. 3, the result show that there is a significant protein expression.

Expression of Epap-1 in Bacteria:

We have cloned the insert into a pET 32 HTa vector in right orientation. For control purpose we have used pET 32 HTb and pET 32 HTc vectors also in cloning. DH5 α bacterial cells were transformed by the cloned vectors following by screening for the insert-containing vector using PCR. The confirmed transformed cells were used for expression of recombinant Epap-1 in BL-21 p-lyse bacterial cells. The expressed protein was purified from the homogenate using Ni-affinity chromatography. The purified protein profile is shown in FIG. 4, the results show that there is high recombinant Epap-1 expression in bacteria.

Analysis of the in vitro Action of the Purified Recombinant Epap-1 on HIV-1 Infection.

The anti-HIV-1 activity of the recombinant was assessed by three screening methods,
1. Binding of Epap-1 to HIV-1 gp120
2. Anti-viral assay in vitro.
3. Inhibition of HIV-1 gp120 mediated cell-fusion by fluorescent dye-transfer bioassay
4. PCR analysis for viral entry.

Screening Method-1

Recombinant baculovirus and bacterial Epap-1 was screened for its binding to gp160 using an ELISA based assay, the results in FIG. 5 show that both the recombinant proteins binds to gp160.

Screening Method 2

HIV-1 infection was conducted in presence of increasing concentrations of Epap-1, the results in FIG. 6 shows that both Baculovirus and bacterial recombinant proteins exhibit significant anti-HIV-1 activity.

Screening Method 3

The action of Native and recombinant proteins on HIV-1 gp120 mediated viral entry was assessed by using a fluorescence dye transfer bioassay. We used 2 dyes calcein AM which shows green fluorescence and Calcein blue which shows a blue fluorescence under our fluorescence microscopic conditions. We used gp120 bearing HL2/3 cells and these cells were loaded with calcein AM cells and the receptors bearing cells used were SUP T1. The SUP T1 cells were loaded with calcein Blue. FIGS. 7, 8 and 9 shows the time course of fusion reaction at 30 minutes (FIG. 7), 60 min (FIG. 8), and 120 min (FIG. 9). The fusion of the two cells and the transfer of green fluorescent dye follow the progress of the reaction in absence of any inhibitor. While in the presence of an inhibitor, cells will be intact and no fusion and dye transfer takes place. Result shown in FIGS. 7, 8, 9 demonstrate that native, baculovirus and bacterial recombinant Epap-1 can completely block HIV-1 gp120 mediated virus entry. We have used CD4 monoclonal SIM4 antibody as positive control in this experiment.

Screening Method 4

The action of Epap-1 in blocking virus entry was further confirmed by analysis of proviral DNA synthesis in an infection conducted in the presence of Epap-1. The cells were challenged with virus in presence of native and recombinant Epap-1. The infected cells were incubated for 5 hours and harvested and proviral DNA was isolated. The isolated proviral DNA was analyzed for the presence of gag regions using gag specific primers SK38 and Sk39 primers through PCR amplification. The results shown in FIG. 10 confirms that Epap-1 can affect proviral DNA synthesis and virus entry.

The results of above screening methods clearly demonstrate that baculovirus and bacterial recombinant Epap-1 possesses significant anti-HIV activity through blocking of virus entry. Hence, the recombinant proteins cloned and expressed are anti-HIV-1 active.

Characterization of Molecular Action of Native and Recombinant Epap-1.

To monitor the interaction of the Epap-1 against virus surface gp120, the HIV-1 virus was incubated with Epap-1. The HIV-1-Epap-1 complexes were captured onto 3T3CD4 cells, using a cell based assay. The epitopes of gp120 on virus surface that are masked in presence of Epap-1 were monitored using various epitope specific monoclonal antibodies of gp160. The results shown in FIG. 11 confirm that native, baculovirus and bacterial recombinant Epap-1 can interact with C5 region of gp120 and this interaction is conserved among 4 HIV-1 virus isolates. In summary, these results confirm a conserved mode of molecular action of native, baculovirus and bacterial recombinant Epap-1 proteins.

Characteristics of Native and Recombinant Epap-1 Proteins

Native Epap-1:

| Properties | Activities |
| --- | --- |
| 90 Kda glycoprotein by SDS PAGE analysis; | Inhibits HIV-1 replication; |
| Binds to *Sambucus nigra* lectin; | Inhibits HIV-1 entry; |
| Binds to Leupeptin and elutes at pH 6 as 60 Kda protein; | Inhibits proviral DNA synthesis; |
| Binds to gp120; | Blocks in a conserved epitopes of gp120 in four HIV-1 virus isolates; |

Recombinant Bacterial Epap-1:

| Properties | Activities |
| --- | --- |
| Expressed in *E. Coli* BL21 cells by bacterial pET 32 HTA vector containing 2330 base pair insert coding for Epap-1 protein and a His tag; | inhibits HIV-1 replication; Inhibits HIV-1 entry, |
| Bacterial recombinant protein of 99 KDa in which Bacterial recombinant Epap-1 is 83 KDa and 16 KDa His tag; | Inhibits proviral DNA synthesis; Blocks in a conserved epitopes gp120 in four HIV-1 virus isolates; |
| Do not Bind to *Sambucus nigra* lectin. Binds to Leupeptin and elutes at pH 6 as 47 KDa protein; Binds to gp120; | |

Recombinant Baculovirus Epap-1

| Properties | Activities |
|---|---|
| Expressed in SF9 insect cells by pFAST Bac HTA vector; | Inhibits HIV-1 replication; |
| Vector contains a 2330 base pair insert coding for Epap-1 protein and a His tag; | Inhibits HIV-1 entry; |
| Bacuclovirus recombinant protein of 99 KDa in which Baculovirus recombinant Epap-1 is 83 KDa and 16 KDa His tag; | Inhibits proviral DNA Synthesis; Blocks in a conserved epitopes of gp120 in four |
| Binds to gp120; | HIV-1 virus isolates; |

Example

The HTA Vector Cloning of Insert DNA:

The appropriate His-Tag vectors were chosen based on the DNA sequence analysis, ORF and orientation. HTa vector and insert DNA in TA Vector was digested with, Sal I and Sac I restriction enzymes for cloning into Baculovirus vector pFast backpack HTa and was digested with Kpn-1 and Sac-1 for cloning into bacterial pET32 HTa vector. The digested DNA was analyzed by 1% agarose gel electrophoresis. The linearized HTa vector and insert DNA was purified by gel extraction. The HTa vector was ligated with insert DNA and ligation mixture was used to transform DH-5 α cells. The transformed colonies were analyzed by colony cracking followed by PCR analysis with M13 primers. The positive colonies were cultured and the recombinant HTa plasmid with insert DNA was isolated. The recombinant baculovirus vector plasmid was used in transposition of DH10 Bac cells. The bacterial recombinant pET32 vector was used to transform BL21 cells for protein expression.

Transposition:

The DH10Bac competent cells were thawed on ice and 100 µl of the cells was dispensed into 15 ml round-bottom polypropylene tubes. Approximately 1 ng recombinant donor plasmid [HTa vector with insert DNA (in 5 µl)] was added and gently the DNA was mixed. The mixture was incubated on ice for 30 minutes. Heat shock was given by transferring to 42° C. water bath for 45 sec's. The mixture was chilled on ice for 2 minutes. 900 µl of SOC medium was added and agitated in shaking incubator at 37° C. (200 rpm) for 4 hours. Serial dilution of the cells were spread evenly on LB plates containing (50 µg/ml kanamycin; 7 µg/ml gentamicin; 10 µg/ml tetramycin; 100 µg/ml X-gal; 40 µg/ml IPTG.) and incubated for 24 to 48 hours at 37° C. The colonies were blue/white selected.

Isolation of Recombinant Bacmid DNA

White colonies contain the recombinant Bacmid, and therefore, were selected for isolation of recombinant Bacmid DNA. Before isolating DNA, candidate colonies are streaked to ensure they are truly white. White colonies from a plate with approximately 100 to 200 colonies are selected. 10 white colonies are picked and streaked on to a fresh plates to verify the phenotype and incubated overnight at 37° C. from a single colony confirmed as having a white phenotype on plates containing X-gal and IPTG, a liquid culture setup was dome containing antibiotics (Kanamycin, gentamicin and tetracycline) for isolation of recombinant Bacmid DNA.

A single, isolated bacterial colony was inoculated into 2 ml LB medium supplemented with 50 µg/ml kanamycin; 7 µg/ml gentamicin; 10 µg/ml tetramycin; incubated at 370 C at 250 to 300 rpm for 24 hours to stationary phase, 1.5 ml of culture was transferred to a 1.5 ml eppendorf tube and centrifuged at 14,000-×g for 1 minute. The supernatant was removed by vacuum aspiration and each pellet was resuspended in 0.3 ml of solution I [15 mM Tris HCl (pH 8), 10 mM EDTA, 100 µg/ml Rnase A] and 0.3 ml of solution II [0.2N NaOH, 1% SDS] and gently mix. Incubate at room temperature for 5 minutes. Slowly add 0.3 ml of Sodium Acetate (pH 5.5) and mix gently and incubated on ice for 5-10 minutes. Centrifuged at 14000-×g for 10 minutes. To the supernatant 0.8 ml of isopropanal was added, mixed and incubated on ice for 5 to 10 minutes. Centrifuged at 14000-×g for 15 minutes. To the pellet 0.5 ml of 70% ethanol was added and centrifuged for 5 min at 14000×g the pellet was air dried, dissolved in TE and stored at −20° C.

Transfection of SF9 Cells with Recombinant Bacmid DNA:

9×10$^5$ million cells per 35 mm well was seeded in 2 ml of SF900 II SFM medium the cells were allowed to attach at 27° C. for at least 1 hour. The following solutions were prepared.

Solution A: for each transfection 5 µl of miniprep Bacmid DNA was added into 100 µl SF900 II SFM without antibiotics Solution B: for each transfection 6 µl of CELLFECTIN reagent was added into 100 µl SF900 II SFM without antibiotics The two solutions was mixed gently and incubated for 15 to 45 minutes at RT. The cells were washed once with 2 ml of SF900 II SFM without antibiotics. For each transfection, 0.8 ml of SF900 II SFM to each tube containing the lipid DNA complexes was added. Mixed gently. Aspirate wash media from cells and overlay the diluted lipid DNA complexes on to the cells. The cells were incubated for 5 hrs in 27° C. incubator. The transfection were removed and 2 ml of SF900 II SFM with antibiotics was added and incubated for 72 hours in a 27° C. incubator. The virus was harvested from cell culture medium at 72 hrs post transfection.

Expression and Purification of 6XHis-Tagged Proteins from Baculovirus Infected Insect Cells Under Native Conditions:

5×10$^6$ million sells in 75 cm$^2$ flask was seeded in 10 ml of SF900 II SFM the cells were allowed to attach at 27° C. for at least 1 hour. Aspirated wash media from cells and infected the adhering SF9 cells with recombinant Baculovirus at MOI of 2×10$^7$, the suspension of infected cells at 72 hours was harvested. The transfected cells were then washed with phosphate buffered saline (PBS) and collected them by centrifugation for 5 min at 1000×g. Cells were lysed in lysis buffer (50 mM NaH2PO4, 300 mM NaCl, 10 mM imidazole pH 8.0) supplemented with 1% Igepal CA-630 using 4 ml lysis buffer per 1-2×107 cells, incubated for 10 min on ice. The lysate was centrifuged at 10,000×g for 10 min at 4° C. to pellet cellular debris and DNA. Cleared lysate (supernatant) was saved.

200 µl of 50% Ni-NTA slurry per 4 ml of the cleared lysate was added and mixed gently by shaking (200 rpm on a rotary shaker) at 4° C. for 1-2 h. The lysate-Ni-NTA mixture was loaded into a column in which the outlet is capped. The outlet cap was removed and the column flow-through fraction was collected. Washed twice with 800 µl wash buffer (50 mM NaH2PO4, 300 mM NaCl, 20 mM imidazole pH 8) collecting wash fractions. The protein was eluted 4 times with 100 µl elution buffer (50 mM NaH2PO4, 300 mM NaCl, 250 mM imidazole pH 8). The eluates were collected in four tubes and analyze by SDS-PAGE.

Expression of His-Tagged Protein in Bl-21 and Purification Under Native Conditions Using Ni Column Chromatography The recombinant Pet32 HTa with insert was used to transform BL21 cells. 10 ml of LB (ampicillin (100 µg/ml)) was inoculated with transformed BL21 cells and incubated at 37° C./150 rpm overnight. 100 ml of prewarmed media (with antibiotics) was inoculated with 1 ml of the overnight cultures and grown at 37° C. with vigorous shaking until an OD600 of 0.6 is reached (30-60 min). Expression induced by adding IPTG to a final concentration of 1 mM. Incubate the cultures for an additional 4-5 h. Collect a second 1 ml sample. The cells were harvested by centrifugation at 4000×g for 20 min. Freeze the cells in dry ice-ethanol or liquid nitrogen, or store cell pellet overnight at −80° C. Thaw the cell pellet for 15 min on ice and resuspend the cells in lysis buffer at 2-5 ml per gram wet weight. Add lysozyme to 1 mg/ml and incubate on ice for 30 min. Sonicate on ice using a sonicator equipped with a microtip. (Optional) If the lysate is very viscous, add Rnase A (10 µg/ml) and Dnase I (5 µg/ml) and incubate on ice for 10-15 min. Centrifuge lysate at 10,000×g for 20-30 min at 4° C. to pellet the cellular debris. Save supernatant. Add 1 ml of the 50% Ni-NTA slurry to 4 ml cleared lysate and mix gently by shaking (200 rpm on a rotary shaker) at 4° C. for 60 min. Load the lysate-Ni-NTA mixture into a column with the bottom outlet capped. Remove bottom cap and collect the column flow-through. Wash twice with 4 ml wash buffer; collect wash fractions for SDS-PAGE analysis. Elute the protein 4 times with 0.5 ml elution buffer. Collect the eluate in four tubes and analyze by SDS-PAGE. The proteins were analyzed on 10% SDS-PAGE followed by western Blotting. Where the Monoclonal His-tag antibody and polyclonal Epap-1 antibody was used.

Anti-HIV Activity Assay 0.2 million Sup-T1 cells were seeded in 1% serum containing RPMI 1640 per well in a 96 well tissue culture plate. Increasing concentrations of drug/protein was added, followed by 200 pg virus (HIV-$1_{93IN101}$) was added. After 2 hours the serum was increased to 10%. The plates were incubated at 37° C., 5% $CO_2$ for 96 hours. At the end of the incubation period the viral titer was quantified using p24 antigen capture assay kit. AZT was taken as positive control.

Cell Based ELISA Assay Method

3T3 CD4cells were grown in a 75 $cm^2$ flask. The cells were grown in DMEM medium, supplemented with 10% fetal calf serum, L-glutamine, sodium pyruvate and penicillin/streptomycin at 37° C. in 5% $CO_2$ in air atmospheres. Cells at the log growth phase were harvested from cultures, washed twice in phosphate-buffered saline (PBS) and suspended to the indicated cell density. 200 µl of cell suspension was added to each well of a 96-well clear ELISA plates (poly-D-lysine coated). The plate was centrifuged at 1000 rpm for 10 min using a rotor specifically designed to carry microtiter plates (Heraeus). The supernatants from the wells were carefully removed. The plate was fixed with 0.05% glutaraldehyde or 4% formaldehyde. After washing with PBS containing 0.5% Tween-20 (PBST), non-specific binding sites were blocked by incubation with 200 µl of blocking buffer (PBS containing 3% BSA and 2% NGS) for 30 min at 37° C. After washing, the cells were incubated with 50 µl of HIV-1/gp120 complexed with Epap-1 (0, 50, 100, 150 ng) for 1 hr at 37° C. After washing, 50 µl of various epitope specific gp120 Monoclonal antibodies (1/1000, 0.75 µg/ml) {(C1 reactive (B2-FNMW, 94-97), C2 reactive (B13-TQLLLN, 257-262), C5 reactive 670-30D, V2 domain reactive 697-30D, V3 Loop reactive (III-V3-21, SVEINCTRPNNNTRKSI, 296-315), V3 domain reactive (257-DIV), (III-V3-13, IRIQRGPGR, V3 PEPTIDE), V4 domain reactive (B15), CD4 reactive (SIM4)} were incubated for 1 hr. After washing, 50 µl of the goat-anti-mouse IgG conjugated to peroxidase (1/1000, 0.75 µg/ml) was added and incubated for 1 hr min at 37° C. The plate was washed and TMB substrate (50 µl) added and incubated at room temperature. The reaction was stopped by adding 50 µl of 2N $H_2SO_4$. The absorbance was read using an ELISA plate reader (Softmax 190, Molecular Devices) at 450 nm.

Epap-1-gp160 Binding Assay:

Mouse monoclonal anti-human gp160 antibodies spanning different regions of HIV-1 gp160 were added into 96 well RIA plate wells at 10 ng per well in PBS {(C1 reactive (B2-FNMW, 94-97), C2 reactive (B13-TQLLLN, 257-262), C5 reactive 670-30D, V2 domain reactive 697-30D, V3 Loop reactive (III-V3-21, SVEINCTRPNNNTRKSI, 298-315), V3 domain reactive (257-DIV), (III-V3-13, IRIQRGPGR, V3 PEPTIDE), V4 domain reactive (B15), CD4 reactive (SIM4)}, the plates were incubated overnight. Following day the wells were blocked with 3% BSA for 2 hours at 37° C., binary complexes containing gp160-Epap-1 were formed by incubation of gp160 in PBS with increasing concentrations of Epap-1 at 37° C. far 1 hour. Binary complexes were captured with gp160 monoclonal antibody pre-coated wells (as above) and incubated for 1 hour at 37° C. The unbound complexes were removed by washing thrice with wash buffer. Captured binary complexes were probed for the Epap-1 using 10 ng of affinity purified Rabbit polyclonal anti-human Epap-1 antibody by incubating for 1 hour at 37° C. and wells were washed thrice with wash buffer. Bound rabbit polyclonal was probed with 1:2000 dilution of Goat anti-rabbit IgG-peroxidase antibody by incubating at 37° C. for 30 minutes, the wells were washed thrice with wash buffer and developed with TMB substrate system. The reaction was stopped after 30 min with 1N HCl and plates were read at 450 nM. Each experiment was done in triplicates and average and standard deviations were calculated.

HIV-1 Entry Inhibition Analysed by Proviral DNA Amplification by PCR:

Analysis of Proviral DNA

SupT1 cells ($0.4 \times 10^6$) were challenged with HIV-$1_{93IN101}$ (100 pg) in presence of increasing concentrations of drugs (1 nM, 10 nM, 100 nM, 1 µM, 10 µM) at 5% $CO_2$ and 37° C. The cells were harvested after 5 hr.p.i and washed with phosphate-buffered saline. The cells were lysed with 50 µl lysis buffer containing 10× Solution A (1M KCl, 100 mM Tris-HCl (pH 8.3), 2.5 mM $MgCl_2$), 10× Solution B (100 mM Tris-HCl (pH 8.3), 2.5 mM $MgCl_2$, 0.45% Tween 20, 045% Nonidet P 40), 50 mM NaCl. The cell lysates were treated with RNaseI (10 µg/ml) and incubated at 37° C. for 30 minutes. Proteinase K (60 µg/ml) was added to the lysates and done each one cycle of PCR (Robocycler 96 from Stratagene, USA) at 56° C. for activation and 95° C. for inactivation of Proteinase K. The lysates were stored at −20° C. until used for PCR (Secondo Sonza et al, 1996).

PCR Analysis of Proviral DNA

The cell lysates were added to the 50 µl of reaction mixture comprising of 10×PCR buffer, 0.2 mM of each deoxynucleoside triphosphate (dNTPs), 2.5 mM $MgCl_2$, 0.40 µM SK38, SK39 sense and anti-sense primers (supplied by integrated DNA Technologies, USA) and 0.5 U of Taq DNA Polymerase (Biogene, USA) (Saiki et al, 1988). The mixtures were heated to 94° C. for denaturation for 2 minutes and then subjected to annealing for 30 cycles of PCR (1 minute, 1 minute and 1.30 minutes for each step of 94° C., 60° C., and 72° C. respectively). After a final extension at 72° C. for 10 minutes. The same samples were amplified with β-actin, which served as an internal control (Kwan et al, 2001). The products were analyzed by agarose gel electrophoresis, Ethedium bromide stained and photographed.

Dye Transfer Fusion Assay

Calcein AM labeling (ex/em 496/517): HL2/3 cells expressing gp120 on surface were incubated with 0.5 µM of Calcein AM for 1 hour at 37° C., washed, incubated in fresh medium for 30 minutes at 37° C., washed and then resuspended 1 million cells/ml.

Calcein Blue loading (ex/em 354/469): Sup T1 cells were loaded with 20 μM of calcein blue for 1 hour at 37° C., washed, incubated in fresh medium for 30 minutes at 37° C., washed and then resuspended 1 million cells/ml.

Fusion assay: fluorescently labeled gp120-41 expressing cells (HL2/3) and CD4⁺ cells (Sup T1) were co-cultured at 1:1 ratio for 2 hours at 37° C. the fusion inhibition was checked in presence of Epap-1 at 100 ng/ml. Fluorescent images were acquired Leica Fluorescent Microscope.

Genebank reference (GenBank accession no. 781142 DQ 357069) for the sequence mentioned at Page 4 under FIG. 12 in section sequencing of insert DNA of positive cDNA clone.

I claim:

1. An anti HIV-1 active human recombinant Epap-1 expressed in bacteria or baculovirus which significantly binds to gp120 of HIV-1 virus isolates.

2. The anti HIV-1 active recombinant Epap-1 as claimed in claim 1, wherein said Epap-1 is expressed in *E.coli* BL21 cells by bacterial pET 32 HTA Vector.

3. The anti HIV-1 active recombinant Epap-1 as claimed in claim 2, wherein said vector contains 2330 base pair insert coding for Epap-1 protein, taken from SEQ ID NO:1, and a polyhistidine tag.

4. The anti HIV-1 active recombinant Epap-1 as claimed in claim 2, wherein said bacterial recombinant Epap-1 protein is 99 KDa and in which 16 KDa is polyhistidine tag.

5. The anti HIV-1 active recombinant Epap-1 as claimed in claim 2, wherein said Epap-1 is expressed in SF9 insect cells by Pfast bas HTA vector.

6. A method for expressing an anti-HIV-1 active recombinant Epap-1 by creating a vector containing 2330 base pair insert coding, taken from SEQ ID NO:1, and a polyhistidine tag, and expressing said vector in *E.coli* cells.

7. An isolated nucleic acid comprising a nucleic acid sequence of SEQ ID NO:1.

8. A vector comprising the nucleic acid of claim 7.

9. The vector of claim 8, wherein the vector is a pET 32 HTA Vector.

10. The vector of claim 8, wherein the vector is a Bacmid.

11. An microorganism comprising the vector of claim 8.

12. The microorganism of claim 11, wherein the microorganism is a baculovirus.

13. The microorganism of claim 11, wherein the organism is a bacteria.

14. The microorganism of claim 13, wherein the organism is an *E. coli* BL21.

15. An isolated recombinant protein comprising an amino acid sequence encoded by the nucleic acid of claim 7.

16. The nucleic acid of claim 7, further comprising a polyhistidine tag.

* * * * *

UNITED STATES PATENT AND TRADEMARK OFFICE
CERTIFICATE OF CORRECTION

| | | |
|---|---|---|
| PATENT NO. | : 7,927,831 B2 | Page 1 of 1 |
| APPLICATION NO. | : 11/885128 | |
| DATED | : April 19, 2011 | |
| INVENTOR(S) | : Kondapi | |

It is certified that error appears in the above-identified patent and that said Letters Patent is hereby corrected as shown below:

On the title page item (54) and col. 1, line 1,

In the Title: insert --ACTIVE-- after "ANTI-HIV-1"

Title Page, References Cited, OTHER PUBLICATIONS, third reference, Kondapi et al., after "activity of" insert --a--

Claim 1, col. 11, line 40, delete "Epap-1" and insert --Early pregnancy associated protein (Epap 1)-- therefor Claim 11, col. 12, line 45, "An microorganism" should read --A microorganism--

Claim 13, col. 12, line 48, "wherein the organism" should read --wherein the microorganism--

Claim 14, col. 12, line 50, "wherein the organism" should read --wherein the microorganism--

Signed and Sealed this
Twenty-seventh Day of September, 2011

David J. Kappos
*Director of the United States Patent and Trademark Office*